Jan. 6, 1959 R. V. SCHREINER Plant Pat. 1,793
IRIS PLANT
Filed May 14, 1958
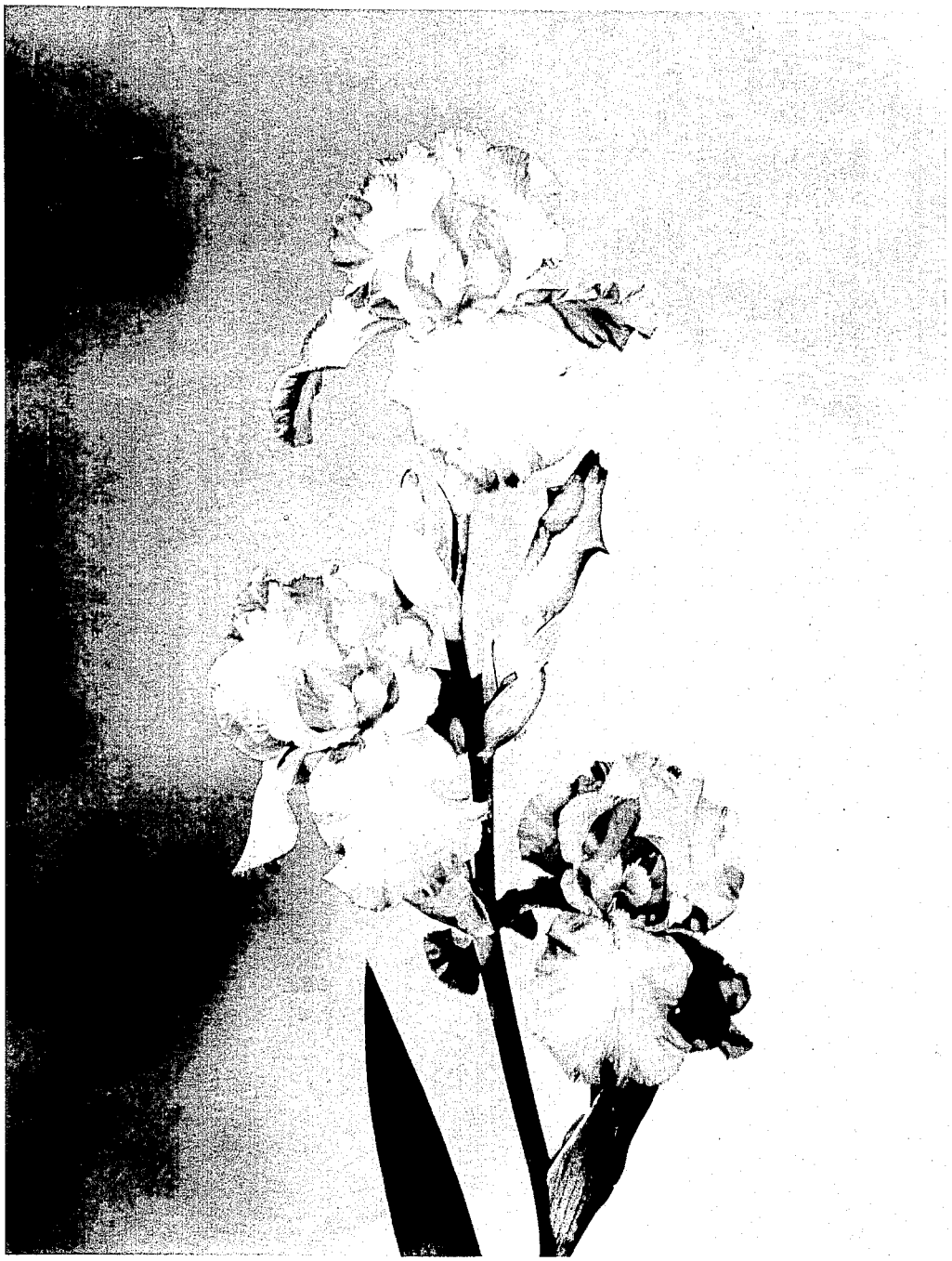
INVENTOR:
ROBERT V. SCHREINER
BY Lummus and Snow
ATT'YS United States Patent Office Plant Pat. 1,793
Patented Jan. 6, 1959

1,793
IRIS PLANT

Robert V. Schreiner, Salem, Oreg.

Application May 14, 1958, Serial No. 735,346
1 Claim. (Cl. 47—60)

My present discovery relates to a new and distinct variety of iris plant which was developed on my breeding plot in Salem, Oregon, through a succession of crosses, the variety "Crispette" (unpatented) being crossed with a seedling of "Lavanesque" (unpatented) crossed with the variety "Pathfinder" (unpatented).

The main result of this invention is the creation of a new iris which possesses certain desired characteristics of the parent varieties and provides a marked improvement in the progeny. These characteristics have been maintained by asexual propagation in quantity production by division of the rhizomes performed by me at Salem, Oregon.

The distinctive features of this new variety are its prolific production of giant blooms of extraordinary substance, and ruffling; its predominately amethyst coloring not previously known in tall bearded iris; its vigorous growth; plentiful number of branching stems which results in an unusual number of widely spaced flowers; and the long-lasting qualities of its blooms.

The accompanying illustration shows, in approximately true colors, a stem with three open flowers, two buds, and a portion of a tip of a foliage blade.

This new variety of iris is beautifully formed with broad gracefully cupped or arching upper petals or standards and moderately flaring falls. Both standards and falls are distinguished by a conspicuously deep ruffling for an iris, this ruffling extending from the edge inward for approximately three-quarters of an inch. The texture, or substance, of the petals of this new iris is unusually heavy (which characteristic lasts for the entire life of the bloom), withstanding all elements equally well, whether heat, wind, or rain. Freedom from floppiness of the petals results from their exceptionally heavy substance and the strong, upright stems. Both the standards and falls have a glistening, lacquered sheen. Below the surface the color saturation is such as to create unusual opaqueness.

In the following detailed description, color plate references indicate Ridgway's Color Standards and Nomenclature, while other colors refer to the ordinary dictionary meaning of the terms.

*Plant*

Growth: Vigorous; stems well branched.
Form: Mound form.
Blooms: Late midseason.
Stems: Approximately deep dull Yellow Green (No. 2) (Plate XXXII). Strong and exceptionally heavy, rising upright to a height of approximately 38 inches. Much branched with side branches ranging from 9 inches on the lower part of stem to 5 inches on upper part of stem.
Foliage: Width—approximately 2½ inches. Rising in mound form, and substantially 29 inches in height.
Color: Medium glaucous green typical of most tall bearded iris; specifically French Green (Plate XXXII). Retention of foliage color is extra good throughout the growing season until late fall.

*Flower*

Bud:
*Size.*—Approximately 1½ inches long when color first shows, expanding rapidly until the day before unfolding into flower, the buds are approximately 4 inches in length.
*Opening.*—Grows slowly until color shows, whereupon it develops rapidly.

*Color.*—Matthew's Purple at tip (Plate XXV) when bud first shows color, lightening to Chinese Violet (Plate XXV) immediately before unfolding into the flower.
*Spathe.*—Light green, the papery portion being Pale Chalcedony Yellow (Plate XVII).

Bloom:
*Size.*—Approximately 7 inches from top to bottom, and 7½ inches from side to side.
*Form.*—Classical; spherical, though slightly broader than high.
*Keeping qualities.*—Each flower lasts approximately 3 days, and a single stem with its side branches will remain in bloom for 2–3 weeks.
*Blooming habit.*—Unusually floriferous and long-lasting. Each stem (with its side branches) bears 11 to 12 buds and blooms.
*Color.*—Predominating color of both upper and lower petals is approximately halfway between Lilac and Chinese Violet (Plate XXV). A narrow edging of Ferruginous (Plate XIV) appears on the haft near the center of the flower. The beard is an off-white (white faintly tinted Mauvette (Plate XXV)).
*Fragrance.*—Mild.
*Form of petals.*—Standards are broadly cupped or arching; falls are of modified flaring form. Both standards and falls are distinguished by an unusually heavy ruffling.
*Size of petals.*—Both standards and falls are approximately 4 inches from claw to tip and approximately 4 inches wide, which is an unusual width for an iris.

Genital organs:
*Pistil.*—Style arms, 3; same color as flower.
*Stamens.*—Filaments, 3. 1½ inches long. Anther approximately ½ inch long. Color: light yellow.
*Pollen.*—Very little pollen. Color: creamy white. Moderately fertile.

The two varieties of iris which most nearly approach my new variety in appearance are "Crispette" (unpatented) and "Orchid Ruffles" (unpatented).

The principal differences are as follows:

My new variety of iris is larger than "Crispette" and much larger than "Orchid Ruffles," and has broader petals and has notably heavier substance than either of them.

My new variety is heavily ruffled, whereas "Crispette" has an unruffled tailored form and the ruffling of "Orchid Ruffles" is scarcely noticeable, being confined to the extreme edge. In contrast, the ruffling of my new variety extends inward three-quarters of an inch from the edge.

My new variety is slightly taller than "Crispette" and approximately six inches taller than "Orchid Ruffles."

My new variety has better branching than either "Crispette" or "Orchid Ruffles."

My new variety differs in color from both of these varieties, being more violet than "Crispette" and less silvery than "Orchid Ruffles." Likewise, "Crispette" is pinker and "Orchid Ruffles" is greyer than my new variety.

Having thus disclosed my invention, I claim:

A new and distinct variety of iris plant, substantially as herein shown and described, characterized particularly by the distinctly glistening sheen of the amethyst coloring of the flowers which are exceptionally large in size and nearly spherical in form; pronounced ruffling of the outer edges of the petals; the heavy texture of the blooms which resists the elements; the large, firm gracefully cupped standards and semi-flaring falls; its height and well-spaced stem-branching; broad foliage, and ease of propagation.

No references cited.